US009029096B2

(12) United States Patent
Sharpe et al.

(10) Patent No.: US 9,029,096 B2
(45) Date of Patent: May 12, 2015

(54) ASSAY AND METHOD

(75) Inventors: David Thomas Sharpe, Leeds (GB); Morgan Clive Thomas Denyer, Bradford (GB); Diana Anderson, Bradford (GB); Stephen Thomas Britland, Keighley (GB); Rajendran Gopalan, Bradford (GB)

(73) Assignee: The University of Bradford, Bradford, West Yorkshire (GB)

( * ) Notice: Subject to any disclaimer, the term of this patent is extended or adjusted under 35 U.S.C. 154(b) by 1079 days.

(21) Appl. No.: 12/446,885

(22) PCT Filed: Oct. 26, 2007

(86) PCT No.: PCT/GB2007/004082
§ 371 (c)(1),
(2), (4) Date: Jul. 23, 2009

(87) PCT Pub. No.: WO2008/050134
PCT Pub. Date: May 2, 2008

(65) Prior Publication Data
US 2010/0035258 A1  Feb. 11, 2010

(30) Foreign Application Priority Data

Oct. 26, 2006 (GB) .................................. 0621272.4

(51) Int. Cl.
*C12Q 1/00* (2006.01)
*C12N 5/071* (2010.01)
*G01N 33/50* (2006.01)
*G01N 27/447* (2006.01)
*G01N 33/48* (2006.01)
*C12Q 1/68* (2006.01)
*C12N 15/01* (2006.01)

(52) U.S. Cl.
CPC .......... *G01N 33/5047* (2013.01); *G01N 27/447* (2013.01); *G01N 2800/40* (2013.01)

(58) Field of Classification Search
None
See application file for complete search history.

(56) References Cited

U.S. PATENT DOCUMENTS 6,960,327 B2 * 11/2005 Navrotsky et al. ............ 423/130

FOREIGN PATENT DOCUMENTS

| JP | 2001-083120 | 3/2001 |
| JP | 2003-210155 | 7/2003 |
| JP | 2007-024612 | 2/2007 |
| SU | 1532873 A | * 12/1989 |
| WO | WO 87/01948 A1 | 4/1987 |

OTHER PUBLICATIONS

Technology Planning and Management Corporation (TPMC) "Report on Carcinogens Background Document for Broad-Spectrum Ultraviolet (UV) Radiation and UVA, and UVB, and UVC", Meeting of the NTP Board of Scientific Counselors Report on Carcinogens Subcommittee, Dec. 13-14, 2000, 356 pages.*
StoreFixture.com "Eyeglass Case: Square Tower" George Patton Associates, Inc. <url:http://www.storefixture.com/store-fixture.asp?ID=7047>, Jan. 2006, 1 page.*
Najafzadeh, M; Baumgartner, A; Gopalan, R; Davies, JB; Wright, A "In vitro Sensitivities to UVA of Lymphocytes from Patients with Colon and Melanoma Cancers and Precancerous States in the Micronucleus and the Comet Assays" Mutagenesis, May 2012 (published online Dec. 8, 2011), 27(3), pp. 351-357.*
Arlett, CF; Lowe, JE; Harcourt, SA; Waugh, APW; Cole, J; Roza, L; Diffey, BL; Mori, T; Nikaido, O; Green, MHL "Hypersensitivity of Human Lymphocytes to UV-B and Solar Irradiation" Cancer Res, Feb. 1, 1993, 53, pp. 609-614.*
International Search Report for International Application No. PCT/GB2007/004082, mailed May 26, 2008 (5 pages).
Azuma et al. "Comparison of Sensitivity to Ultraviolet B Irradiation Between Human Lymphocytes and Hematopoietic Stem Cells" *Blood* 96(7):2632-2634 (2000).
Munch-Petersen and Frentz. "X-Ray and UV-Radiation Sensitivity of Circulating Lymphocytes in Multiple Epidermal Cancer in Relation to Previous Radiation Exposure" *Radiation Research* 103:432-440 (1985).
Pedeux et al. "Ultraviolet B Sensitivity of Peripheral Lymphocytes as an Independent Risk Factor for Cutaneous Melanoma" *European Journal of Cancer* 42:212-215 (2006).
Wang et al. "In Vitro Sensitivity to Ultraviolet B Light and Skin Cancer Risk: A Case-Control Analysis" *Journal of the National Cancer Institute* 97(24):1822-1831 (2005).
Zana et al. "Alzheimer's Lymphocytes are Resistant to Ultraviolet B-Induced Apoptosis" *Neurobiology of Aging* 27:831-834 (2006).
Anderson et al. "Oestrogenic Compounds and Oxidative Stress (in Human Sperm and Lymphocytes in the Comet Assay)" *Mutation Research* 544:173-178 (2003).
Boyum. "A One-Stage Procedure for Isolation of Granulocytes and Lymphocytes from Human Blood. General Sedimentation Properties of White Blood Cells in a 1 g Gravity Field" *Scandinavian Journal of Clinical and Laboratory Investigation* 97:51-76 (1968).
Boyum et al. "Separation of Human Lymphocytes from Citrated Blood by Density Gradient (NycoPrep) Centrifugation: Monocyte Depletion Depending Upon Activation of Membrane Potassium Channels" *Scand J Immunol* 56:76-84 (2002).
Collins. "The Comet Assay for DNA Damage and Repair: Principles, Applications, and Limitations" *Molecular Biotechnology* 26:249-261 (2004).
De Haes et al. "1,25-Dihydroxyvitamin $D_3$ and Analogues Protect Primary Human Keratinocytes Against UVB-Induced DNA Damage" *Journal of Photochemistry and Photobiology* 78:141-148 (2005).

(Continued)

*Primary Examiner* — Jon P Weber
*Assistant Examiner* — Aaron J Kosar
(74) *Attorney, Agent, or Firm* — Myers Bigel Sibley & Sajovec, P.A

(57) ABSTRACT

The present invention relates to a method and assay useful for determining the sensitivity of the cells of a subject to genetic damage from electromagnetic radiation. The assay may comprise a substrate suitable for mounting a sample of lymphocytes from a subject and an electromagnetic radiation source.

29 Claims, 2 Drawing Sheets

(56) References Cited

OTHER PUBLICATIONS

Garland et al. "Epidemiologic Evidence for Different Roles of Ultraviolet A and B Radiation in Melanoma Mortality Rates" *Ann Epidemiol* 13:395-404 (2003).

Giovannucci. "The Epidemiology of Vitamin D and Cancer Incidence and Mortality: A Review (United States)" *Cancer Causes and Control* 16:83-95 (2005).

Lehmann et al. "UVB-Induced Conversion of 7-Dehydrocholesterol to 1α,25-Dihydroxyvitamin $D_3$ (Calcitriol) in the Human Keratinocyte Line HaCaT" *Photochemistry and Photobiology* 72(6):803-809 (2000).

Lehmann et al. "UVB-Induced Conversion of 7-Dehydrocholesterol to 1α,25-Dihydroxyvitamin $D_3$ in an In Vitro Human Skin Equivalent Model" *The Journal of Investigative Dermatology* 117(5):1179-1185 (2001).

Levi et al. "Trends in the Incidence of Various Morphologies of Malignant Melanoma in Vaud and Neuchatel, Switzerland" *Melanoma Research* 15:73-75 (2005).

Liu et al. "Alterations of DNA Damage-Response Genes *ATM* and *ATR* in Pyothorax-Associated Lymphoma" *Laboratory Investigation* 85:436-446 (2005).

Lovell et al. "Issues Related to the Experimental Design and Subsequent Statistical Analysis of In Vivo and In Vitro Comet Studies" *Teratogenesis, Carcinogenesis, and Mutagenesis* 19:109-119 (1999).

MacKie. "Awareness, Knowledge and Attitudes to Basal Cell Carcinoma and Actinic Keratoses Among the General Public Within Europe" *JEADV* 18:552-555 (2004).

Meewes et al. "Adaptive Antioxidant Response Protects Dermal Fibroblasts From UVA-Induced Phototoxicity" *Free Radical Biology & Medicine* 30(3):238-247 (2001).

Rafferty et al. "Effects of Selenium Compounds on Induction of DNA Damage by Broadband Ultraviolet Radiation in Human Keratinocytes" *British Journal of Dermatology* 148:1001-1009 (2003).

Sander et al. "Role of Oxidative Stress and the Antioxidant Network in Cutaneous Carcinogenesis" *International Journal of Dermatology* 43:326-335 (2004).

Schallreuter et al. "In Vivo and In Vitro Evidence for Hydrogen Peroxide ($H_2O_2$) Accumulation in the Epidermis of Patients With Vitiligo and its Successful Removal by a UVB-Activated Pseudocatalase" *JID Symposium Proceedings* 4(1):91-96 (1999).

Singh et al. "A Simple Technique for Quantitation of Low Levels of DNA Damage in Individual Cells" *Experimental Cell Research* 175:184-191 (1988).

Soufir et al. "Association Between INK4a-ARF and p53 Mutations in Skin Carcinomas of Xeroderma Pigmentosum Patients" *Journal of the National Cancer Institute* 92(22):1841-1847 (2000).

Tice et al. "Single Cell Gel/Comet Assay: Guidelines for In Vitro and In Vivo Genetic Toxicology Testing" *Environmental and Molecular Mutagenesis* 35:206-221 (2000).

Young. "Chromophores in Human Skin" *Phys Med Biol* 42:789-802 (1997).

Zak-Prelich et al. "Environmental Risk Factors Predisposing to the Development of Basal Cell Carcinoma" *Dermatol Surg* 30(2):248-252 (2004).

Ohyama et al. "DNA Damage and Apoptosis" *Journal of Clinical and Experimental Medicine* 187(5):363-367 (1998) (12 pages including translation).

Marrot et al. "Photostability of sunscreen products influences the efficiency of protein with regard to UV-induced genotoxic or photoageing-related endpoints" *British Journal of Dermatology* 151:1234-1244 (2004).

X. F. et al. "Effect of Antioxidants on UV-Induced DNA Breakage in Human Peripheral Lymphocytes" *Bulletin of Environmental Contamination and Toxicology* 59:888-893 (1997).

* cited by examiner

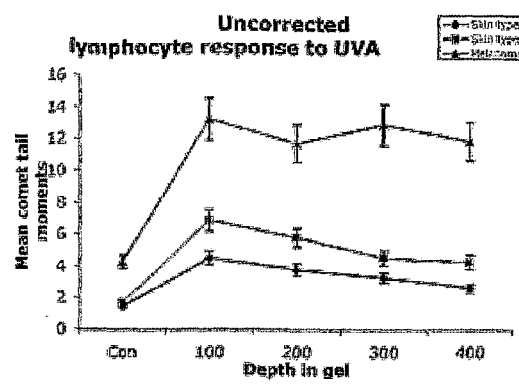
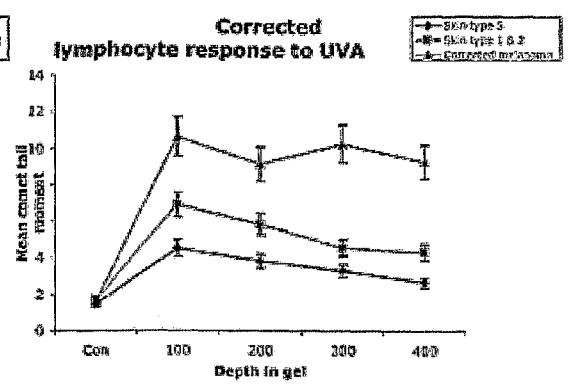
Fig. 1a  Fig. 1b
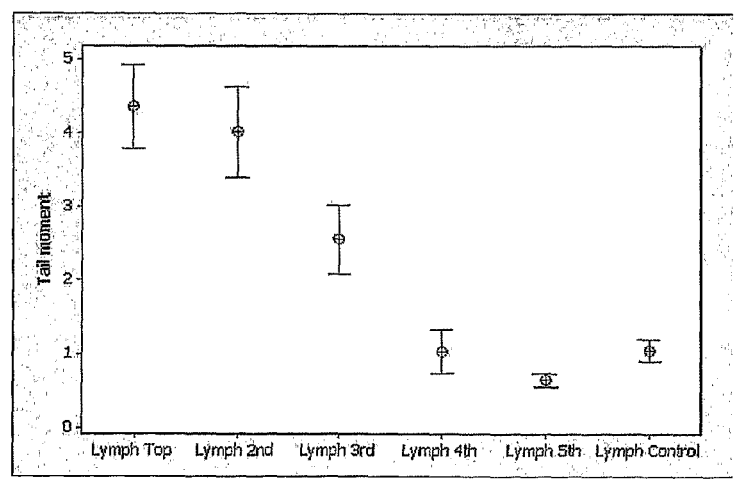
Fig. 2

ASSAY AND METHOD

This application is a 35 U.S.C. § 371 national phase application of PCT Application Ser. No. PCT/GB2007/004082, filed Oct. 26, 2007, which claims priority to Great Britain Application No. 0621272.4, filed Oct. 26, 2006, the entire contents of each of which are incorporated by reference herein.

The present invention relates to assays and methods useful for determining the sensitivity of a subject to electromagnetic (EM) radiation induced, especially ultraviolet radiation (UV) induced, cellular damage. In particular, the assays and methods have utility in determining a subject's sensitivity to sun-induced genetic damage which may potentially lead to skin cancer. Other related methods and assays are also provided.

UV absorption generates oxygen derived free radicals inducing DNA damage via the production of a range of photoproducts[1]. This process can change the base pairing abilities of normal DNA resulting in mutations. It is these mutations that may lead to skin cancers because they disrupt tumour suppressor genes such as P53, and INK4A[2]. Free radicals also play a role in a whole range of other cancers. There is evidence that free radical related mutations of the ATM (Ataxia-telangiectasia mutated) and ATR (Rad3-related) genes play a role in lymphomagenesis[3]. In terms of skin cancer, modern travel trends and climatic changes have significantly heightened the exposure of millions of people to UV irradiation and the incidence of skin cancers. As a result of this, awareness about the harmful effects of exposure to the sun has increased, and via messages contained within public awareness campaigns like the "slip slap slop" programme, exposure to UV irradiation has decreased. Unfortunately, there is a very odd anomaly associated with this. Despite the heightened awareness and avoidance of UV exposure, the incidence of skin cancers has continued to increase[4, 5, 6].

Skin has an elegant way of coping with UV irradiation. UV exposure initially decreases antioxidant activity[11] and after UV irradiation increases antioxidant up-regulation[12], increases melanogenesis and the conversion of 7-dehydrocholesterol to vitamin D3. Vitamin D3 can then be hydroxylated directly in the skin by keratinocytes into 25(OH)D, which can then be further hydroxylated by the keratinocytes into the most active form of vitamin D, 1α-25(OH)2D13. The antioxidants (including catalase, superoxide dismutase, glutathione reductase/peroxidase, thioredoxin reductase/thioredoxin/thioredoxin peroxidase, melatonin and its metabolites and photodegradants) counter the production of free radicals, so a decrease in antioxidant activity during UV irradiation is at first unexpected. It would seem logical to expect antioxidant activity to increase, thus decreasing the damaging effect of UV induced free radicals. However, on consideration the decrease in antioxidant activity may be very important in that it ensures that any free radical-related genomic damage is lethal to the cell. This would predispose any cell suffering UV related damage to become terminally differentiated and subsequently remove itself and its damaged genome from the skin. Associated with this removal of damaged cells, there is an up-regulation of specific kinases, for example MAPK (mitogen activated protein kinase) which probably has a role in aiding the replacement of damaged cells and increasing skin thickness. In this system the increased melanin production functions as a sun screen and vitamin D, locally activated in the skin, acts initially as a site specific anti cancer agent by promoting terminal cell differentiation, and inhibiting cell proliferation[14], which of course further accelerates the loss of UV damaged cells. It is apparent that UVB exposure sufficient to induce the minimal reddening (minimal erythemal dose, MED) induces the localised production of vitamin D at a level of 100 times the normal recommended dose for an adult[15]. Melanin's peak UV absorption occurs at 335 nm[16] in the UVA spectrum and where expected if the system has evolved to block the most energetic UVA wavelengths. There is also evidence that peak UV related vitamin D production occurs in keratinocytes at 297 nm[17], a wavelength located in the UVB tail of the melanophores UV absorption spectrum. Thus it seems that melanophores block the most damaging UVA wavelengths, whilst enabling some UVB related vitamin D production. This system functions via positive and negative feedback mechanisms and as such can almost be considered as a self regulating "smart sensor". As melanin is up-regulated, the skin tans, this then blocks UV-related cell damage and also decreases vitamin D production, whilst at the same time enabling antioxidant activity to increase again. Unfortunately it is possible to overload this system, thus additional UV protection becomes important.

A key issue in providing the required UV protection is the determination of individual sensitivity to the sun. This is difficult to achieve, and is currently done using qualitative methods involving looking at skin type (type 1-5), skin, hair, eye coloration, looking at family history and incidence of skin cancer, and by counting the number of moles already present on the skin. However, sensitivity is probably at least partially genetically governed, so what is required is a quantitative assay that can define an individuals genomic sensitivity to the sun.

Sun creams block UVA and UVB. UVB has a low penetrance in skin, just about extending to the basal layer of the epidermis, it promotes tanning and provides one of the major sources of vitamin D. UVB directly produces hydrogen peroxide in the skin in a dose dependent manner and also causes damage in skin cells and lymphocytes[18, 19]. It is probable that the majority of commercially available sun creams block vitamin D production. UVA has a much higher penetrance of skin, it promotes tanning and also has a damaging effect on the genome of skin cells, but UVA has no effect on vitamin D concentrations. There is epidemiological evidence that worldwide, UVA exposure is more closely associated with the incidence of melanoma than UVB[20].

Historically, sun creams have focused on UVB because UVB induces the skin reddening associated with overexposure. UV sun creams are tested and SPFs (Sun Protection Factor) calculated by determining the time it takes to induce this minimal reddening in fair skinned type one individuals. This provides limited information about the damaging effects of UVA. This is a problem that may be overcome by the modern generation of suncreams aimed at blocking both UVA and UVB, however it would be very useful if these new systems were assayed in relation to their ability to directly block genomic damage. Indeed, there is currently no satisfactory way of assessing the performance of such sun creams in preventing UV-induced genomic damage.

Current means of predicting susceptibility to UV induced skin damage (e.g. melanoma) are primarily based on determination of the presence of certain mutations in genes associated with UV sensitivity. The problem with such assays is that they are, by their nature, currently restricted to a relatively small number of genes identified as having a role in skin cancer. It is extremely unlikely that all genes involved in UV sensitivity will be identified in the near future and, even if they were, it would be an onerous task to examine each and every one for deleterious mutations. There will always be doubt with such assays as to whether other contributing factors, be they undiscovered genes or unrelated mechanism, have a role in cellular UV sensitivity.

Although UV is of particular interest, being a significant factor in skin cancer, other types of electromagnetic radiation are also of interest. For example, the effects of X-rays, microwave radiation, gamma rays and other types of EM radiation on cells are currently not well understood.

Thus there is a need for assays which may be used to quantitatively evaluate the sensitivity of an individual to genomic damage by EM radiation, especially UV radiation, and that might also provide a means to assay the efficacy of sun creams or other protective materials in preventing such damage.

Over the past decade, the Comet assay, or single-cell gel electrophoresis assay has become one of the standard methods for assessing DNA strand breaks in cells[7]. Cells embedded in agarose on a microscope slide are lysed with detergent and high salt concentration to form nucleoids containing supercoiled loops of DNA linked to the nuclear matrix. Electrophoresis at high pH>13[8] results in structures resembling comets, observed by fluorescence microscopy in which the intensity of the comet tail relative to the head reflects the number of DNA strand breaks and alkali labile sites. Loops containing a break lose their supercoiling and freely move towards the anode[9]. Thus the Comet assay provides a means of determining genomic damage.

According to the present invention there is provided an assay to determine the sensitivity of the cells of a subject to genetic damage from electromagnetic (EM) radiation, the assay comprising:
  a substrate suitable for mounting a sample of lymphocytes from said subject; and
  an EM radiation source.

Preferably the source of EM radiation is a source of UV radiation.

It has been discovered that an assay in which lymphocytes are exposed to UV radiation provides a very good indication of the cellular sensitivity of a subject to UV-induced genetic damage. The results of an assay on lymphocytes shows a remarkable correlation with the sensitivity of a subject's skin to UV-induced damage and thus provides a useful basis for advising on sun protection and other UV avoidance measures. Thus the assay is preferably suitable for determining the sensitivity of skin cells of a subject. The assay according to the present invention not only enables the quantitative evaluation of individual genomic sensitivity to the sun, but can also be used to assess the genomic protective qualities of new sun creams or other protective materials or compositions.

The assay preferably comprises a sample of lymphocytes from said subject mounted on said substrate. There is a significant advantage in using lymphocytes rather than skin cells (e.g. melanocytes or keratinocytes) in such an assay; skin cells are generally difficult to obtain, requiring a biopsy of some sort (e.g. a punch biopsy), whereas a blood sample is very easy to obtain (e.g. through standard phlebotomy, a pin prick or, conveniently, obtained when blood is donated). Additionally, the techniques used for the isolation of lymphocytes is routine.

By the term lymphocyte it is meant that any large granular lymphocytes and/or the small lymphocytes may be used in the present assay. In particular, natural killer cells and/or T and/or B lymphocyte may be used. Suitably a mixture of 70% to 80% large granular lymphocytes and small lymphocytes and 15% to 30% monocytes may be used.

Generally the substrate has a planar surface for mounting the cells. It will typically be made of a material which is bio-compatible with lymphocytes and is substantially resistant to EM radiations damage at the frequency and intensity used in the assay, e.g. UV resistant. Suitable substrates include a glass, plastic or metal slide, or a silicon chip. A preferred substrate is glass, such as a glass microscope slide or the like.

It should be noted that there is often a need to automate and increase throughput of assays and, in that case, a suitable substrate may be a microfluidics-based array or microarray of some type, for example a spot array on a glass slide or a silicon chip. Thus, the present assay is readily amenable to such automation.

Suitably the lymphocytes are mounted on the substrate in a mounting medium, and accordingly the assay of the present invention may comprise a mounting medium. The mounting medium may be any substance which is substantially permeable to EM radiation (typically UV) and which is suitable for lymphocytes to adhere to, or reside within, without causing significant damage to said lymphocytes. A particularly suitable mounting medium is agarose gel, though other gels, culture media or suchlike known in the art of cell handling or culturing, may be equally suitable. Mounting the lymphocytes in such a medium has an advantage in that it replicates to some extent the anatomical reality that cells are embedded below the surface of the skin. Furthermore, when a test substance such as a sun cream is applied on top of such a medium it will tend to be partially absorbed by the medium, thus mimicking the way sun cream is partially absorbed by the skin.

It is generally preferred that the cells are contained predominantly within the mounting medium. This is readily achieved when the cells are suspended or embedded in agarose gel or other such gels.

It is particularly preferred that the cells are mounted in a medium which is suitable for performing electrophoresis. Agarose gel is, of course, particularly suitable for this purpose, as may be other gels such as polyacrylamide or alginate. Such a medium allows a comet assay, preferably a 3D comet assay, to be conveniently used to determine the extent of genetic damage to said cells following EM radiation exposure.

Suitably the mounting medium is agarose gel of, having from 0.1 to 5% agarose concentration. More preferably the mounting medium is low melting point agarose (LMA— available, for example, from Invitrogen).

Suitably the assay comprises an EM radiation-permeable (typically UV-permeable) barrier material suitable to be interposed between the sample of lymphocytes and the ultraviolet radiation source. Such a barrier is valuable in that it may serve to replicate the shielding or absorbing function of the outer layers of skin which lie above the living skin cells in a subject. The EM radiation-permeable barrier is typically a substance which allows at least a portion of the radiation to pass through it to the sample of lymphocytes. The role of the barrier is to emulate to some extent the upper layers of the skin which absorb at least a portion of the sun's radiation. The barrier may be made of any suitable material which may be formed into a layer and which allows a portion (e.g. from 1 to 99%, more preferably from 10 to 90%) of EM radiation to pass therethrough. In a laboratory setting suitable materials include gels, for example an agarose gel, a polyacrylamide gel, an alginate gel or other such gel. A particularly preferred gel is a low melting point agarose (LMA) gel which can be formed on top of the sample of lymphocytes once they have been mounted on the substrate. It is generally convenient if the EM radiation-permeable barrier material is formed from the same substance as the mounting medium. An alternative material which would emulate the role of the surface layers of skin is a sample of real or artificial skin, optionally impregnated with keratin or melanin.

In one embodiment the EM radiation-permeable barrier is built up as a laminate structure composed of layers of the same or differing materials. Suitably the barrier is made up of layers of from about 10 μm to 100 μm in thickness to give a total barrier thickness of from about 10 μm to 1000 μm. The layers are conveniently made of agarose gel or other suitable gel materials.

In a preferred embodiment the assay comprises from 1 to 10 layers of an EM radiation-permeable barrier, each layer being from 10 μm to 100 μm thick. The assay may suitably comprise a plurality of lymphocyte samples each having a different thickness (e.g. number of layers) of EM radiation-permeable barrier provided on them. The total thickness of barrier(s) thus suitably ranges between 10 μm and 1000 μm thick, preferably from 10 μm to 500 μm. By varying the thickness of the EM radiation-permeable barrier, the penetrative effects of the EM radiation can be assessed. Regions of varying thickness of UV-permeable barrier may be provided on the same substrate.

Using such an EM radiation-permeable barrier allows additional information regarding the sensitivity of the cells to be obtained. The manner in which the UV-induced damage is reduced as the thickness of the barrier increases seems to vary between different subjects. For example, cells which are obtained from melanoma patients do not show a typical depth related reduction in UV-induced genetic damage. Other patterns of changing sensitivity relative to depth for certain cell types can be observed. This effect is of significant diagnostic value.

Furthermore, using a number of different thicknesses of EM radiation-permeable barrier effectively provides an internal control. By observing a pattern of changes relative to depth, rather than simply an absolute value for damage at a single depth, it is possible to establish that the assay has performed correctly. An error such as an excessive radiation dose would effect the pattern and be clearly identifiable, whereas if a single value were taken, there would be no way of identifying such an error. Systems of internal control are extremely important in diagnostic assays where the reliability of the result is paramount.

The UV radiation source is suitably able to emit UV radiation at least partially within the range of UV present in solar radiation. The UV radiation source may suitably be able to emit both UVA (380-315 nm, also called Long Wave or "blacklight" UV) and UVB (315-280 nm, also called Medium Wave UV). However, in some embodiments it may not be necessary for the UV radiation source to emit radiation across such a broad range, and accordingly a source of either UVA or UVB only, or indeed even UV of a narrow range of wavelengths, may be perfectly suitable for use in the assay. In one suitable embodiment the UV radiation source emits UVA, which is particularly suitable as it is UVA which is understood to be the most closely linked with the incidence of melanoma. In this case an exemplary suitable UV source is a UV lamp such as the Waldmann UVA lamp (Athrodax Healthcare International Ltd) though other such lamps are widely available. It may, however, be preferred that the UV radiation source is able to substantially mimic the UV spectrum and intensity of solar radiation experienced at the Earth's surface (this would of course vary at different altitudes, latitudes and other deferring environmental conditions).

In one embodiment the assay comprises means to detect genetic damage in said lymphocytes. A number of such means are well known in the art.

In one preferred embodiment the means to detect genetic damage is means to perform a comet assay, more preferably a 3D comet assay. Such means may comprise, for example, a lysing agent to lyse the lymphocytes and an electric source adapted to generate an electric field across at least a portion of a medium in which the cells are mounted.

Alternatively the means to detect genetic damage may be adapted to detect specific mutations in the sample of lymphocytes. Suitable means may include, for example, hybridisation assays, PCR based assays (e.g. PCR apparatus and suitable primers to analyse an area of interest) and in vivo/in vitro assays.

Of course, it will be understood that there are many means for detecting specific or non-specific genetic damage in cells, many of which will be suitable for use in the present invention, and the above are recited solely as exemplary of what is currently envisaged as being the most suitable for use in the present invention.

Suitably the subject is a mammal, preferably a primate, particularly a human.

The assay may further comprise means to provide a test substance between the sample of lymphocytes and the EM radiation source. Suitable test substances include a sun cream or sun block, a layer of fabric, polymer or glass. Particularly envisaged are fabric for clothing and polymeric or glass lenses for glasses. The means to provide the test substance may conveniently be the surface of the mounting medium, e.g. for the application of a fluid test substance, e.g. a cream or lotion. Such fluid test substances may alternatively be applied to a substrate such as a glass slide or other UV-permeable surface, though this is generally less preferred as such substrates are generally not able to allow a portion of the test substance to be absorbed, as is the case in reality with skin. Alternatively, the means may be a frame, platform or other such substrate to mount a solid test substrate.

The assay may further comprise a test substance providence between the sample of the lymphocytes and the UV radiation source.

In a further aspect the present invention provides a method of assaying the sensitivity of cells (especially skin cells) of a subject to genetic damage from electromagnetic (EM) radiation, the method comprising:

mounting a sample of lymphocytes from said subject on a substrate;
  irradiating the sample of lymphocytes with EM radiation; and
  detecting genetic damage in at least a portion of the sample of lymphocytes.

Preferably the EM radiation is UV radiation.

The sample of lymphocytes may conveniently be mounted on said substrate in a mounting medium as set out in more detail above.

The method preferably comprises providing an EM radiation-permeable barrier on or adjacent to the sample of lymphocytes. Accordingly, in this embodiment, the EM radiation irradiates the cells through the EM radiation-permeable barrier. The step of providing EM radiation-permeable barrier may comprise of providing one or more layers of the barrier material on the mounted sample of lymphocytes. Accordingly, the thickness of the EM radiation-permeable barrier can be determined by the number of layers provided.

Generally non-specific genetic damage or genetic damage at a particular site or region may be detected. In general it is preferred if non-specific genetic damage is detected as this will provide an indication of overall genetic damage. In a particular preferred embodiment the method comprises detecting genetic damage via a comet assay, more preferably via a 3D comet assay in which genetic damage can be assayed in situ in the mounting medium.

Alternatively, or additionally, genetic damage may be detected at particular sites or regions in the genome. Sites or regions of particular interest may be those containing or which are associated functionally or positionally with tumour suppressor genes (TSGs) or oncogenes, particularly those associated with skin cancer. Relevant TSGs or oncogenes will be apparent to the person skilled in the art, but example would be the TSGs encoding p-53, INK4A and pRb, and the oncogenes src and ras. Other genes which may be of interest include ATM and ATR.

The length of time the lymphocytes are exposed to the EM radiation is not generally critical, and will depend on the intensity and type of the EM radiation and the amount if EM radiation absorbed by mounting medium, EM radiation-permeable barrier and the like. However, it should be noted that the period should be sufficient to generate detectable levels of genetic damage within the sample of lymphocytes, but not so extreme that the cells are damaged to such an extent that sensitivity of the assay is reduced, e.g. if the samples is so damaged that it is not possible to determine differences between different skin types. Generally the level of exposure should be sufficient to induce levels of genetic damage which are detectable, especially through a comet assay.

The method may comprise obtaining a sample of lymphocytes from a subject. This may be achieved by taking a blood sample or, conveniently, by taking a sample from donated blood.

The method may further comprise comparing the genetic damage of the test sample with a set of predetermined values to accesses the subject's sensitivity to EM radiation-induced genetic damage relative to a standard or average value, or set of values. This effectively allows the subject to be graded depending on their relative skin sensitivity and advised accordingly on what protective or prophylactic measures may be required to prevent or reduce excessive cellular damage.

The method may further comprise providing an EM radiation-permeable barrier, essentially as described previously.

The method may further comprise providing a test substance, essentially as described previously.

In a further aspect, the present invention provides an assay to determine the ability of a test substance to prevent EM radiation induced damage to the cells of a subject, the assay comprising;
 a substrate suitable for mounting a sample of lymphocytes from said subject;
 a source of EM radiation; and
 means for providing a test substance between said EM radiation source and said substrate.

Other optional features of the assay, e.g. EM radiation-permeable barrier and suitable mounting media etc. are as described earlier.

In a further embodiment the present invention provides a method of determining the ability of a test substance to prevent EM radiation induced damage to the cells of a subject, the method comprising:
 mounting a sample of lymphocytes from said subject on a substrate;
 providing an EM radiation source;
 providing a sample of said test substance between said EM radiation source and said sample of lymphocytes;
 activating said source of EM radiation such that said test substance is irradiated and radiation passing through said substance irradiates said sample of lymphocytes; and
 detecting genetic damage to the lymphocytes.

Preferably the test substance is a sun cream or sun block.

Alternatively the test substance may be a layer of fabric, polymer or glass. Particularly envisaged are fabric for clothing and polymeric or glass lenses for glasses. However, it will be understood that the present method and assay is suitable for determining the ability of essentially any material for its protective effect against UV damage.

The sample of test substance may conveniently be applied to the surface of cells mounted on the substrate, for example spread or placed on the surface of a mounting medium.

In a further aspect the present application provides the use of an assay or method as described above in a method of determining the predisposition of a subject to developing cancer or in diagnosing cancer in a subject.

In a preferred embodiment, the method is for the determining the predisposition to developing, or diagnosing, a skin cancer, especially melanoma.

The method may suitably involve comparing the results of the assay with predetermined values, or patterns of values, and determining from the comparison the relevant result.

Although the assay has been shown to have powerful diagnostic value in relation to melanoma, it has also been shown that it's utility extends beyond this into other forms of cancer.

The present invention will now be further described, by way of example only, with reference to the following examples and the accompanying figures in which:

FIGS. 1a and 1b show a graph of UV damage for a number of different skin types relative to their depth (in µm) in agarose gel.

FIG. 2 shows the 95% CI plot for UV exposure related comet tail moment (with 50 cells per treatment repeated twice, n=100) for lymphocytes embedded in different depths of agarose.

EXAMPLE 1

Skin Type Assay

Figure 3:
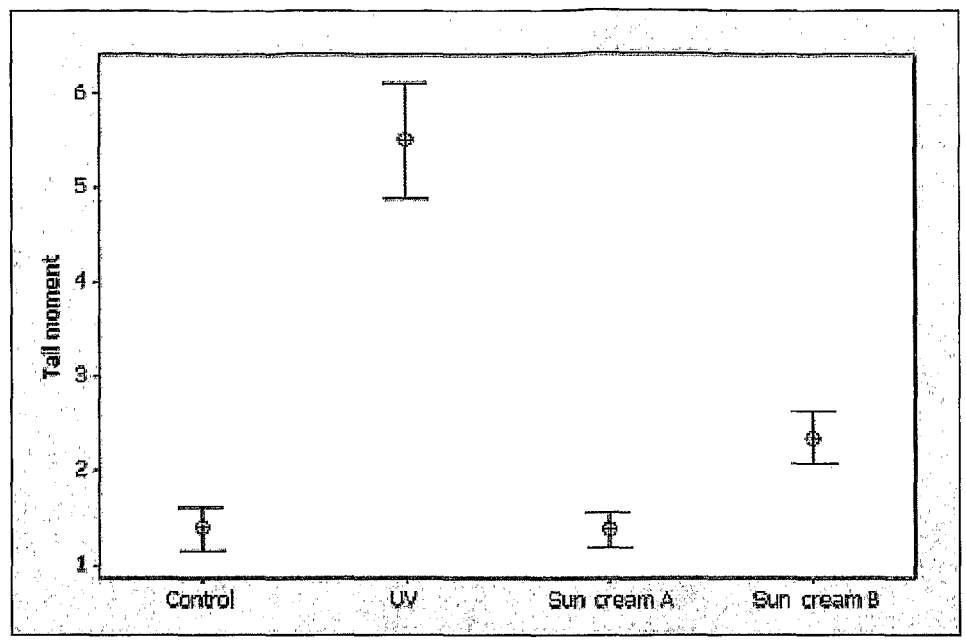
FIG. 3 shows a 95% CI plot for the comet tail moment for human melanocytes embedded in an agarose gel without UV exposure (Control), cells embedded in the second layer of an agarose gel at a depth of 91 µm and exposed to UVA (UV) for 15 minutes and cells embedded in an agarose gel and protected by Sun cream A and Sun cream B.

This experiment was performed to demonstrate the potential for an assessment of lymphocytes to indicate the sensitivity of a subject's skin cells to UV-induced damage.

Methods

To test this the genomic responses to UVA of lymphocytes was assessed. The lymphocytes were derived from:
 Melanoma patients.
 Skin type 5 individuals (Black African subjects who never burn but always tan).
 Skin type 1 and 2 subjects (Caucasian subjects who always burn, but never tan (1), or tan slowly (2)).

The lymphocytes derived from the Black African subjects can be considered as being representative of the lowest sensitivity to UV related genomic damage, whilst the lymphocytes from skin type 1 and 2 subjects functions as a measure of the upper normal genomic UV sensitivity. As a negative control lymphocytes were embedded in the gel at a depth of 100 µm and processed without UVA irradiation.

The lymphocytes were embedded at different depths in an agarose gel. The assay was carried out essentially as set out for the depth of penetration assay which is described in Example 2. The methods are not repeated here for brevity.

Results

The results of these experiments showed that even with blood samples collected from a relatively small number of subjects (11 subjects per sub group), there were significant differences between the responses to UV irradiation of cells derived from the skin type 1 and 2 subjects, the skin type 5 subjects and the melanoma patients (FIG. 1a and Table 2). Of the three subgroups, the lymphocytes from the skin type 5 subjects showed the lowest sensitivity in relation to UV irradiation, whilst the lymphocytes from the skin type 1 and 2 subjects showed a significantly increased ($P \leq 0.01$) comet tail moment in response to UVA irradiation. However, both the lymphocytes from the healthy skin type 1 and 2 and skin type 5 subjects displayed comet tail moments that declined significantly ($P \leq 0.01$) in relation to depth in the gel. In comparison, the lymphocytes derived from the melanoma patients showed a greatly increased mean comet tail moment in response to UVA irradiation which did not decline significantly in relation to depth in the gel.

However, the melanoma patients also showed an elevated control mean comet tail moment of almost twice that of the skin type 1 and 2 and skin type 5 subjects. This may reflect the fact that the melanoma patients were in receipt of treatment, or that the melanoma patient samples had been stored for up to 6 months in liquid nitrogen, both factors may have increased the background genomic damage. To correct for this, the mean increase in comet tail moment for the melanoma patients control treatment was calculated and subtracted from the comet tail values for the control and depth related UV exposure treatments of lymphocytes derived from the melanoma patients (FIG. 1b). This correction had little effect on the overall trend, melanoma patients still had a significantly increased UV related mean comet tail moment when compared with the skin type 1 and 2 subjects ($P \leq 0.01$), which did not decline greatly when compared with the mean comet tail moments of lymphocytes derived from skin type 1 and 2 subjects and skin type 5 subjects.

Interestingly some anomalous data was acquired, indicating very strongly that sensitivity to UV irradiation cannot be simply assessed from phenotype (Skin, hair and eye colour). One skin type 1/2 subject displayed a genomic response as determined via the comet tail assay that looked very similar to a melanoma patient's response. On questioning it was discovered that this subject had had a pre-cancerous mole removed. Also one phenotypically skin type 5 individual showed a genomic response to UV that looked very similar to a skin type 1 and 2 individual. On questioning it was discovered that this subject originated from the Caribbean. In the Caribbean the population is mostly of mixed race, thus it is probable that this subject although having a very dark skin had inherited a gene resulting in an increased sensitivity to UV irradiation.

The variation in individual sensitivity to UV irradiation is probably associated with inherited genetic mutations associated with the up or down regulation of proteins that play a role in the genomic repair mechanism. One would assume that these mutations arose in the Caucasian population and as such have, up until relatively recent evolutionary history, been confined to this group. This may no longer be the case.

TABLE 1

Mean comet tail moments from melanoma patients, skin type 1 and 2 subjects, skin type 5 subjects and the corrected melanoma patients.

| Variable | No of subjects | Mean comet tail moments | SE |
| --- | --- | --- | --- |
| Melanoma control | 11 | 4.25 | 0.46 |
| Melanoma 100 μm | 11 | 12.26 | 1.09 |
| Melanoma 200 μm | 11 | 11.76 | 0.94 |
| Melanoma 300 μm | 11 | 12.91 | 1.28 |
| Melanoma 400 μm | 11 | 11.89 | 1.37 |
| Skin type 1&2 control | 11 | 1.70 | 0.23 |
| Skin type 1&2 100 μm | 11 | 6.89 | 0.34 |
| Skin type 1&2 200 μm | 11 | 5.81 | 0.45 |
| Skin type 1&2 300 μm | 11 | 4.53 | 0.42 |
| Skin type 1&2 400 μm | 11 | 4.29 | 0.50 |
| Skin type 5 control | 11 | 1.47 | 0.19 |
| Skin type 5 100 μm | 11 | 4.51 | 0.29 |
| Skin type 5 200 μm | 11 | 3.81 | 0.28 |
| Skin type 5 300 μm | 11 | 3.29 | 0.25 |
| Skin type 5 400 μm | 11 | 2.65 | 0.28 |
| Corrected melanoma control | 11 | 1.59 | 0.46 |
| Corrected melanoma 100 μm | 11 | 10.59 | 1.09 |
| Corrected melanoma 200 μm | 11 | 9.10 | 0.94 |
| Corrected melanoma 300 μm | 11 | 10.24 | |
| Corrected melanoma 400 μm | 11 | 9.23 | 1.40 |

Discussion

These preliminary experiments strongly suggest that melanoma patients have an increased sensitivity to UV related genomic damage and that this heightened sensitivity can be determined via the lymphocyte assay. The data also strongly indicates that one cannot rely on phenotype (skin colour etc) to predict UV sensitivity and that individuals who by skin coloration would be considered to be at low risk, genetically may in actual fact be at high risk. This is of particular importance and clearly shows the need for an assay that can be used to quantify individual susceptibility to UV induced melanoma. The present assay fulfils this requirement and may in the long term play a very significant role in reversing the ever-increasing incidence of melanoma in the population. The present assay provides a very useful tool in better informing individuals of their specific risks of skin cancer. The assay is remarkable in that it uses a non-skin cell to determine the sensitivity of a subject's skin to UV damage. This makes the assay simpler and less invasive than one which involves obtaining skin cells. Additionally, the assay, by virtue of not using skin cells, is not significantly affected by recent skin exposure to UV, and thus provides a true indication of inherent skin sensitivity.

The assay is remarkable as it exploits an unexpected correlation between UV sensitivity in different cell types, particularly lymphocytes and skin cells. This correlation is unexpected, and suggests that there is a common system running throughout cells to mitigate UV-induced damage. This is surprising as one would naturally expect that only skin cells would be under pressure to exhibit such mechanisms of defence.

EXAMPLE 2

Depth of UV Penetration in Relation to Comet Tail Moment

This experiment was performed to accesses the role of depth of cells within agarose (i.e. a UV-permeable barrier) relative to UV-induced genetic damage.

Methods 12 superfrosted 76×26 mm slides (BDH) were sterilised in 70% ethyl alcohol and flamed. Each slide was dipped in 1% normal melting point agarose (NMA, Invitrogen) and wiped to remove the agarose from the underside. The slides were air dried overnight at 500° C. Twelve eppendorf tubes with 100 µl of 20,000 cells/ml of a human lymphocyte suspension were prepared and equal volumes of 1% low melting point agarose (LMA, Invitrogen) was added to each. 100 µl of the cell suspension/LMA mixture from each eppendorf was placed on each NMA agarose pre-coated slide. A 22×50 mm coverslip was used to flatten the LMA/cell agarose layer before each slide was transferred to an ice block. After five minutes the coverslip was removed and a further 100 µl layer of 0.5% LMA was added to each slide and a cover slip was once again used to flatten the LMA resulting in this building up to 91 µm deep. Additional layers of LMA were added to build up agarose layers of 182 µm, 273 µm and 364 µm over the cells. The coverslips were removed and discarded and 2 slides were used to generate controls (no UV irradiation), the remaining 10 slides (2 slides per agarose thickness) were exposed to UVA for 15 minutes via a Waldmann UVA lamp (Athrodax Healthcare International Ltd) at a mean sample surface intensity of 1.53±0.01 mWcm$^2$. The mean intensity of the applied UVA light was determined by measured UVA intensity using a Waldmann Variocontrol UV meter (Athrodax Healthcare Internatiol Ltd) from 10 different positions under the UVA lamp.

After UVA treatment the slides were transferred to a lysing solution at pH 10 (2.5M NaCl, 100 mM EDTA and 10 mM Tris buffer all made up to 700 ml and then supplemented with 1% Triton X-100 and 10% DMSO (SIGMA)) and incubated overnight at 4° C. After incubation, the slides were rinsed in distilled water and placed in an electrophoresis tank filled with buffer (consisting of 60M NaOH+200 mM EDTA+distilled H2O at pH 10) and left in the fridge for thirty minutes to allow unwinding of the DNA. The slides were subjected to electrophoresis for 30 mins at a constant voltage (25V).

The slides were finally transferred to a washing tray and given three washes at intervals of five minutes with a neutralising buffer (0.4M Tris pH adjusted to 7.5 with HCl) and stained with ethidium bromide (20 µg/ml—Invitrogen). Comets tail moments were determined by transferring the slides to a fluorescent microscope (Lieca DMLB) and viewed via a 20× epi-flourescent objective (Lieca). Digital images were acquired via a Kinetic Imaging K2 CCD camera and 100 comet tails per treatment were automatically scored using Komet 4 (Kinetic Ltd. Liverpool). Statistical analyses were performed using MINITAB.

Results

The 3D Comet assay consists of a system in which cells are embedded in multiple layers of agarose, thus allowing examination of the UV related genomic damage in relation to depth of UV penetration. This was tested with a modified assay with human lymphocytes (FIG. 2), irradiating cells on the surface of the gels, and embedded in 91 µm, 182 µm, 273 µm and 364 µm thick layers of agarose and examined at comet tail moments associated with each treatment against a control (no UVA irradiation). As expected, it was found that UV related genomic damage decreased in relation to depth of agarose, such that, by a depth of 273 µm comet tail moment had returned to control levels. The results are summarised below. Similar results have been shown with frozen/thawed lymphocytes and cells from the HaCat keratinocyte cell line (data not shown).

TABLE 2

Summarised data from UV penetration assay

| Position | Comment | Mean comet tail moment ± S.E |
|---|---|---|
| Top | no additional layers of agarose | 4.35 ± 0.28 |
| 2nd | 91 µm thick layer of agarose over the cell layer | 4.00 ± 0.31 |
| 3rd | 182 µm thick layer of agarose | 2.55 ± .23 |
| 4th | 273 µm thick layer of agarose | 1.03 ± 0.15 |
| 5th | 364 µm thick layer of agarose | 0.65 ± 0.05 |
| Control | no UV irradiation | 1.04 ± 0.07 |

EXAMPLE 3

Sun Cream Treatment

This experiment was performed to evaluate the efficacy of two commercially available sun creams (both SPF 30 and designed to block UVA and UVB) in preventing UV-induced genetic damage.

Methods 16 superfrosted 76×26 mm slides (BDH) were prepared and human melanocytes were embedded in agarose at a depth of 91 µm as described above. NB, although melanocytes are used in the present example, it would be preferable, and perfectly feasible, to use lymphocytes. To assess the blocking abilities of the two commercially available sun creams, 100 µl of each sun cream was applied to the gel surface of 4 coated slides per sun cream whilst they were maintained at 4° C. The 8 slides were UVA irradiated, incubated and scored as above. 4 negative controls were produced by embedding, incubating and scoring in the absence of UVA and 4 positive controls were generated by UVA irradiation in the absence of any sun cream. Scoring of 200 cells per treatment was achieved as described above.

Results

Human melanocytes were then used in the assay embedded at a depth of 91 µm to assess the efficacy in relation to UVA protection of two well known "Kids" sun creams (sun cream A and sun cream B), both claiming an SPF of 30 and an ability to block UVA and UVB. Reproducible experiments (FIG. 3) with 100 cells per treatment (two slides with 50 scored cells per slide) repeated twice (n=200) showed that the negative control (Control), non-UVA exposed human melanocytes, had a mean comet tail moment of 1.39±0.10. In comparison, the positive control (UV), UVA exposed cells, showed a mean comet tail moment of 5.50±0.31. When compared with positive and negative controls these experiments showed that the application of sun cream A returned the comet tail moment to negative control levels, 1.38±0.10, whilst sun cream B did not, resulting in a mean comet tail moment of 2.34±0.14. Analyses of data pooled from 4 separate slides per treatment can lead to another view of the data[10], thus the data was also interrogated by acquiring the mean comet tail moments for each slide and calculating the mean of the 4 means per treatment. This method of analyses has no effect on the calculated means, but can greatly change the standard errors. By doing this it was found that the standard error for the control treatment remained unchanged at 0.10, but the standard errors for the UV exposed, sun cream A and sun cream B increased to 0.91, 0.14, and 0.18 respectively. However, these increases in standard errors made no difference in terms of interpreting the data. The mean comet tail moments for the negative control and sun cream A remain insignificantly different from one another, whilst the mean comet tail moments for the negative control, the positive control and sun cream B are all significantly different from one another. Although only two sun creams were compared, these results strongly suggest that UVA/UVB blocking sun creams with supposedly the same SPFs provide different levels of UVA protection.

EXAMPLE 4

Further Skin-Type Assay Investigations

Figure 4:
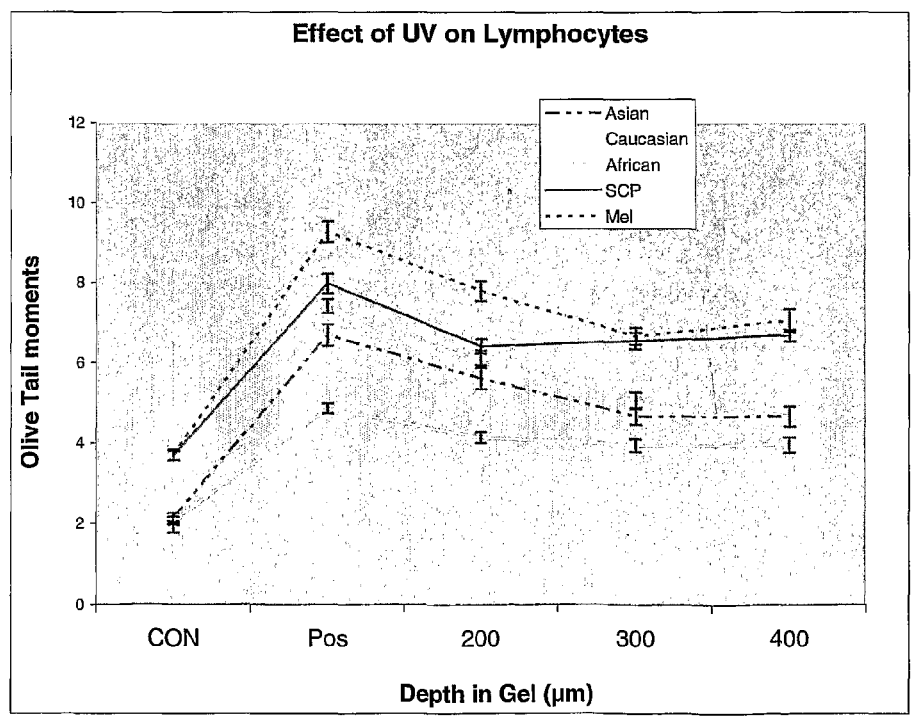
FIG. 4 shows a graph of the UVA/depth related Comet tail moments of freshly collected lymphocytes derived from diagnosed melanoma (Mel) patients, suspected melanoma patients (SCP), Black African, Asian and Caucasian subjects.

Further tests were conducted to assess the effects of UV irradiation on lymphocytes embedded at different depth using lymphocytes freshly collected from suspected melanoma patients. The inventors examined the effects of UV irradiation via the comet assay using lymphocytes derived from Caucasian (n=20), Asian (n=20) and Black African subjects (n=20), and lymphocytes freshly collected from suspected melanoma patients (SCP, n=22). Of this last group, eight were subsequently diagnosed as suffering from melanoma and were thus considered separately from the suspected melanoma patients. As a negative control, lymphocytes were embedded in the gel at a depth of 100 μm and processed without UVA irradiation. The results of these experiments indicate that lymphocytes from melanoma patients have significantly greater sensitivities to UV irradiation than lymphocytes derived from suspected, but non-melanoma patients, Caucasians, Asians and Black African subjects and that this sensitivity, initially declined in relation to the depth before increasing again at depths of 400 μm in the gel. The suspected melanoma patients in comparison displayed a lower sensitivity to UVA irradiation, but this sensitivity did not decline significantly in relation to depth, and at depths of 300 and 400 μm were lower but statistically similar to the responses of lymphocytes derived from the melanoma patients (FIG. 4). The sensitivities of lymphocytes derived from the Caucasian, Asian and Black African subjects were all significantly different from one another, but unlike the suspected melanoma patients and the confirmed melanoma patients, their Comet tail moments declined significantly in relation to depth in the gel.

These results strongly indicate that there is a correlation between the incidence of melanoma and increased UVA sensitivity as assessed by the assay of the present invention, and that the assay can be used to identify those at increased risk of developing melanoma.

Although the experiments detailed above relate primarily to UV radiation, it is fair to conclude that other types of EM radiation could be assaying in a similar manner, and their effects on cellular genetic damaged assessed.

REFERENCES

[1] T. S. Rafferty, M. H. L. Green, J. E. Lowe, C. Arleft, J. A. A. Hunter, G. J. Beckett, R. C. McKenzie, Effects of selenium compounds on induction of DNA damage by broadband ultraviolet radiation in human keratinocytes. Br. J. Dermatol. 148 (2003) 1001-1009.

[2] N. Soufir, L. Daya-Grosjean, P. de la Salmoniere, J. P. Moles, L. Dubertret, A. Sarasin, N. Basset-Seguin, Association between INK4a-ARF and p53 mutations in skin carcinomas of xeroderma pigmentosum patients. J. Natl. Cancer I. 92 (2000) 1841-1847.

[3] A. Liu, T. Takakuwa, S. Fujita, M. F. Ham, W. J. Luo, M. Daibata, K. Aozasa, Alterations of DNA damage-response genes ATM and ATR in pyothorax-associated lymphoma. Lab. Invest. 85 (2005) 436-446.

[4] F. Levi, V. Te L. Randimbison, C. La Vecchia, Trends in incidence of various morphologies of malignant melanoma in Vaud and Neuchatel, Switzerland. Melanoma Research 15 (2005) 73-75.

[5] R. M MacKie, Awareness, knowledge and attitudes to basal cell carcinoma and actinic keratoses among the general public within Europe. J Eur Acad Dermatol 18 (2004) 552-555.

[6] M. Zak-Prelich, J. Narbutt, A. Sysa-Jedrzejowska, Environmental risk factors predisposing to the development of basal cell carcinoma. Dermatol. Surg 30 (2004) 248-252.

[7] R. R. Tice, E. Agurell, D Anderson, B. Burlinson, A. Hartmann, H. Kobayashi, Y. Miyame, E. Rojas, J. C. Ryu, Y. F. Sasaki, Single Cell Gel/Comet Assay: Guidelines for In Vitro and In Vivo Genetic Toxicology Testing. Environ. Mol Mutagen 35 (2000) 206-221.

[8] N. P. Singh, M. T. McCoy, R. R. Tice, E. L. Schneider, A simple technique for quantitation of low levels of DNA damage in individual cells. Exp.Cell Res, 175 (1988) 184-191.

[9] A. R. Collins, The Comet assay for DNA damage and repair: principles, applications and limitations. Mol. Biotechnol. 26 (2004) 249-261.

[10] D. P. Lovel, G. Thomas, R. Dubow, Issues related to the experimental design and subsequent statistical analyses of in vivo and invitro comet studies. Teratog, Carcenog, Mutogen. 19 (1999) 109-119.

[11] C. S. Sander, H. Chang, F. Hamm, P. Elsner, J. J. Thiele, Role of oxidative stress and the aptioxidant network in cutaneous carcinogenesis, Int. J. Dermatol. 43 (2004) 326-335.

[12] C. Meewes, P. Brenneisen, J. Wenk, L. Kuhr, W. J. Ma, J. Alikoski, A. Poswig, T. Krieg, K. Scharffetter-Kochanek, Adaptive antioxidant response protects dermal fibroblasts from UVA-induced phototoxicity. Free Radical Bio Med. 30 (2001) 238-247.

[13] B. Lehmann, T. Genehr, P. Knuschke, J Pietzsch, M. Meurer, UVB-induced conversion of 7-dehydrocholesterol to $1\alpha,25$-dihydroxyvitaminD$_3$ in an in vitro human skin equivalent model. J. Invest. Dermatol. 117 (2001) 1179-1185.

[14] P. De Haes, M. Garmyn, A. Verstuyf, P. De Clercq, M. Vandewalle, H. Degreef, K. Vantieghem, R. Bouillon, S. Segaert, S. 1,25-Dihydroxyvitamin D-3 and analogues protect primary human keratinocytes against UVB-induced DNA damage. J. Photochem. Photobiol. B 78 (2005) 141-148.

[15] E. Giovannucci, The epidemiology of vitamin D and cancer incidence and mortality: A review(United States). Cancer Causes and Control 16 (2005) 83-95.

[16] K. U. Schalreuter, J. Moore, J. M. Wood, W. D. Beazley, D. C. Gaze, D. J. Tobin, H. S. Marshall, A. Panske, E. Panzig, N. A. Hibberts, In vivo and in vitro evidence for hydrogen peroxide ($H_2O_2$) accumulation in the epidermis of patients with vitiligo and its successful removal by a UVB-activated pseudocatalase. J. Invest. Dermatol. Symposium Proceedings. 4 (1999) 91-96.

[17] A. R. Young, Chromophores in human skin. Phys. Med. Biol, 42 (1997) 789-802.

[18] B. Lehmann, P. Knuschke, M. Meurer, UVB-induced conversion of 7-dehydrocholesterol to 1 alpha,25-dihydroxyvitamin D-3 (calcitriol) in the human keratinocyte line HaCaT, Photochem. Photobiol. 72 (2000) 803-809.

[19] D. Anderson, T. E. Schmid, A. Baumgartner, E. Cemeli-Carratala, M. H. Brinkworth, J. M. Wood, Oestrogen compounds and oxidative stress (in human sperm and lymphocytes in the comet assay). Mutation Res. 544 (2003) 173-178.

[20] C. F. Garland, F. C. Garland, E. D. Gorham, Epidemiologic evidence for different roles of ultraviolet A and B radiation in melanoma mortality rates. Ann. Epidemiol. 13 (2003) 395-404.

[21] Boyum, A., Brincker Fjerdingstad, H., Martinsen, I., Lea, T., Lovhaug, D. Separation of humanlymphocytes from citrated blood by density gradient (NycoPrep) centrifugation: monocyte depletion depending upon activation of membrane potassium channels. Scand. J. Immunol. 56 (2002) 76-84.

[22] Boyum, A. A one-stage procedure for isolation of granulocytes and lymphocytes from human blood. General sedimentation properties of white blood cells in a 1 g gravity field. Scandinavian Journal of Clinical and Laboratory Investigation. 97 (1968) 51-76.

The invention claimed is:

1. A system for performing an assay to determine the sensitivity of the cells of a subject to genomic damage from electromagnetic radiation, the system comprising:
   a substrate suitable for mounting a sample of lymphocytes from said subject;
   a mounting medium, suitable for performing electrophoresis, for mounting said sample of lymphocytes;
   an electromagnetic (EM) radiation source; and
   an EM radiation-permeable barrier material interposed between the substrate suitable for mourning said sample of lymphocytes and the EM radiation source, wherein the EM radiation-permeable barrier material is a substance which allows at least a portion of the EM radiation to pass through the barrier material to the sample of lymphocytes; where the EM radiation-permeable barrier has regions of different thickness and said regions are arranged to determine patterns of different sensitivity to genomic damage from the EM radiation relative to the thickness.

2. The system of claim 1, wherein the electromagnetic radiation source is an ultraviolet (UV) radiation source.

3. The system of claim 1, comprising the sample of lymphocytes from said subject mounted on said substrate.

4. The system of claim 3, in which the lymphocytes comprise a mixture of 70% to 80% large granular lymphocytes and small lymphocytes and 15% to 30% monocytes.

5. The system of claim 3, wherein the lymphocytes are mounted within said mounting medium and are contained predominantly within the mounting medium.

6. The system of claim 1, wherein the substrate has a planar surface for mounting the lymphocyte cells.

7. The system of claim 1, wherein the substrate is a glass, plastic or metal slide, or a silicon chip.

8. The system of claim 1, wherein the substrate is a microfluidics array or microarray.

9. The system of claim 1, wherein the mounting medium is a gel.

10. The system of claim 1, wherein the EM radiation-permeable barrier is formed at least in part from the same substance as the mounting medium.

11. The system of claim 1, wherein the EM radiation-permeable barrier comprises one or more layers of from 10 μm to 100 μm in thickness to provide a total barrier thickness of from 10 μm to 1000 μm.

12. The system of claim 1, comprising a plurality of lymphocyte samples mounted by the mounting medium to the substrate, each mounted lymphocyte sample having a different thickness of EM radiation-permeable barrier provided thereupon.

13. The system of claim 1, wherein the electromagnetic radiation source is able to emit UV radiation at least partially within the wavelength range of UV present in solar radiation.

14. The system of claim 13, wherein the electromagnetic radiation source is able to emit both UVA and UVB.

15. The system of claim 13, wherein the electromagnetic radiation source emits UVA.

16. The system of claim 13, wherein the electromagnetic radiation source is able to substantially mimic the UV spectrum and intensity of solar radiation experienced at the surface of the earth.

17. The system of claim 1, comprising means to detect genomic damage in said lymphocytes.

18. The system of claim 17, wherein the means to detect genomic damage is means to perform a comet assay.

19. The system of claim 1, further comprising a test substance provided between the substrate and the EM radiation source.

20. The system of claim 19, wherein the test substance is a sun cream or sun block.

21. The system of claim 19, wherein the test substance is a layer of fabric, polymer or glass.

22. The system of claim 19, comprising said sample of lymphocytes mounted on the substrate and/or mounting medium and wherein the test substance is in contact with the surface of said lymphocytes.

23. The system of claim 1, wherein the subject is a human.

24. The method of claim 1, wherein the EM radiation-permeable barrier is composed of multiple layers of the same or different materials.

25. A method of assaying the sensitivity of cells of a subject to genomic damage from electromagnetic (EM) radiation using the system of claim 1, the method comprising:
   mounting a sample of lymphocytes from said subject in the mounting medium;
   providing the EM radiation-permeable barrier on or adjacent to the sample of mounted lymphocytes;
   irradiating the sample of lymphocytes with EM radiation from the EM radiation source; and
   detecting if genomic damage is present in at least a portion of the sample of irradiated lymphocytes.

26. The method of claim 25, wherein the EM radiation-permeable barrier material is interposed between the sample of lymphocytes and the EM radiation source.

27. The method of claim 25, wherein the EM radiation-permeable barrier comprises one or more layers of from 10 μm to 100 μm in thickness to provide a total barrier thickness of from 10 μm to 1000 μm.

28. The method of claim 25, comprising a plurality of lymphocyte samples mounted by the mounting medium to the substrate, each mounted lymphocyte sample having a different thickness of EM radiation-permeable barrier provided thereupon.

29. The method of claim 25, further comprising the step of providing a test substance between the sample of lymphocytes and the EM radiation source.

* * * * *